| United States Patent [19] | [11] Patent Number: 4,588,690 |
| Nissen et al. | [45] Date of Patent: May 13, 1986 |

[54] PREPARATION OF THE ENZYME β-GLUCANASE BY FERMENTATION OF FUNGI

[75] Inventors: Bernt A. Nissen, Stathelle; Jon Hovland, Porsgrunn, both of Norway

[73] Assignee: Norsk Hydro a.s., N-Oslo, Norway

[21] Appl. No.: 642,628

[22] PCT Filed: Dec. 5, 1983

[86] PCT No.: PCT/NO83/00056
  § 371 Date: Aug. 15, 1984
  § 102(e) Date: Aug. 15, 1984

[87] PCT Pub. No.: WO84/02533
  PCT Pub. Date: Jul. 5, 1984

[30] Foreign Application Priority Data
Dec. 22, 1982 [NO] Norway ................................. 824321

[51] Int. Cl.$^4$ .......................... C12N 9/24; C12R 1/785

[52] U.S. Cl. ..................................... 435/200; 435/931
[58] Field of Search .................................. 435/200, 931

[56] References Cited

U.S. PATENT DOCUMENTS 4,110,163  8/1978  Hjortshoj et al. .................. 435/200

FOREIGN PATENT DOCUMENTS 8402533  7/1984  PCT Int'l Appl. .

*Primary Examiner*—Lionel M. Shapiro
*Attorney, Agent, or Firm*—Wenderoth, Lind & Ponack

[57] ABSTRACT

Process for preparation of β-glucanase by cultivation of species of the fungus *Rhizomucor pusillus* (Lindt) Schipper under aerobic and thermophilic conditions. The enzyme β-glucanase is an important component for degradation of polysaccharides into shorter molecular units.

13 Claims, No Drawings

PREPARATION OF THE ENZYME β-GLUCANASE BY FERMENTATION OF FUNGI

The present invention concerns a process for preparation of β-glucanase.

It has long been known that barley has a content of the polysaccharide β-glucan. Barley-β-glucan is structurally a polysaccharide consisting of glucose with β-1,4- and β-1,3-bonds between the glucosidic units, where approximately 70 pph of the bonds are β-1,4-bonds and 30 pph are β-1,3 bonds.

If barley with a high content of β-glucan is used as chicken feed, the chickens get into trouble because their digestive system is not capable of degrading the β-glucan. It passes through the digestive system and comes out as a sticky droppings, and the chickens show symptoms of diarrhoea.

When pure barley is used instead of malted barley for brewing of beer, the wort will be viscous, which makes the filtration of the wort from the mask difficult.

The reason is that unmalted barley only has a small content of the glucandegradable enzyme β-glucanase.

The abovementioned problem can be avoided by adding β-glucanase to the barley, but this is a question of price and for beer-brewing also a question of legislation.

Moreover, it is also a question of cultivating microorganisms which are particularly suited for the production of β-glucanase. It is also a question of the yield of enzymes from and the correct cultivation conditions of the microorganism.

It is known that some microorganisms are capable of producing the enzyme β-glucanase in use for degrading the β-glucan.

UK Pat. No. 1 421 127 describes a method for preparation of β-glucanase suited for degradation of β-glucan in barley when the microorganism *Penicillium emersonii* is used. It is a thermophilic microorganism with an optimum of growing at 50°–54° C. and where the growing is extremely low at temperatures below 37°–40° C. Below optimum conditions the fermentation will last for 7–10 days.

DD Pat. No. 148 891 also describes a process for preparation of β-glucanase, but in this process the microorganism *Bacillus subtilis* is used. The preparation of the enzyme is done under aerobic and submersible conditions in a free flowing nutrient medium at approx. 30° C.

DE patent application No. 2 048 237 describes a process for preparation of β-glucanase by means of the microorganism *Aspergillus phoenicis*. This organism is not described as thermophilic, and the optimum of growing seems to be at 25°–35° C. when grown under aerobic conditions.

The abovementioned known processes have some drawbacks. Firstly, the fermentation lasts too long when the thermophilic microorganism *Penicillium emersonii* is used and secondly the enzyme produced by fermentation of *Penicillium emersonii* and *Bacillus subtilis* will have minimized activity at lower pH. *Aspergillus phoenicis*, as used in the West-German process, cannot be characterized as thermophilic at all, as its optimum of growing will be in the area of 25°–35° C.

It now appears that microorganisms of the species *Rhizomucor pusillus* (Lindt) Schipper satisfy the purpose of the invention because the microorganism is thermophilic, is growing fast and gives a high yield of enzymes in relation to the short time of fermentation.

Species of the said organism have been isolated from earth and from barley grain. One of these has shown to be extremely well suited and is deposited and described as CBS 551.82 at the Centralbureau voor Schimmelcultures, Holland. Further, species of *Rhizomucor pusillus* from the American Type Culture Collection, USA have been tested. The one best suited has the description ATCC 22074. In addition to the significance of the said organism for the good result it should also be mentioned that the composition of the nutrient medium, the support of air and the shape of the fermentation vessel are important factors in order to achieve optimal conditions during the fermentation and in this manner contribute to fulfil the purpose of the invention.

The Nutrient Medium

The fungi mentioned above can be cultivated by growing them on a solid medium, e.g. potatous-dextrose-agar, at 40°–45° C. To produce larger quantities of β-glucanase the fungi have to be transferred to a liquefied medium. A piece of agar of approximately 2×2 $cm^2$ is cut out and homogenized in the well-known way with about 10 ml of the medium. 2 ml of the homogenisat is transferred to sterile 300 ml Erlenmeyer with 100 ml medium As medium is used:

| | |
|---|---|
| Soluble starch | 5,0 g |
| $KH_2PO_4$ | 1,0 g |
| $MgSO_4 \cdot 7 H_2O$ | 0,88 g |
| $CaCl_2$ | 0,1 g |
| Trace elements-solution | 1,25 ml |
| $(NH_4)_2$-tartrate | 3,0 g |
| Aqua dest. | 1,0 l | with pH adjusted to 5,5.

The trace elements-solution consisted of:

| | |
|---|---|
| $H_2SO_4$ conc. | 1,5 ml |
| $CuSO_4 \cdot 5 H_2O$ | 1,0 g |
| $FeSO_4 \cdot 7 H_2O$ | 15,0 g |
| $ZnSO_4 \cdot 7 H_2O$ | 6,2 g |
| $MnSO_4 \cdot H_2O$ | 1,5 g |
| Aqua dest. | 1,0 l |

The Erlenmeyers are incubated at 40° C. by shaking until fair growth is achieved after 48–72 h. 300 ml of the inoculum is transferred to a 7 l fermenter with 5 l salt medium of the following composition:

| | |
|---|---|
| $KH_2PO_4$ | 2,0 g |
| $MgSO_4 \cdot 7 H_2O$ | 1,75 g |
| $CaCl_2$ | 0,2 g |
| Trace elements-solution | 2,5 g |
| Water | 1,0 l |

The trace elements-solution has the same composition as the one described above.

The medium also contains a substrate which supplies the fungus with the necessary energy and carbon together with a nitrogen source.

Different energy and carbon sources are used during the growth, of which common potato flour, barley flour and cornflour are most suitable.

The flour is added in relation to the oxygen transferring capacity of the fermenter in such a way that the culture always is under an aerobic condition.

The following may be used as suitable N-sources: $KNO_3$, $NH_4Cl$ and urea. The nitrogen source is added in relation to the amount of carbon in such a way that the weight proportion between carbon and nitrogen is not more than 7, preferably 3-7, more preferably about 5.

The fermenter must be equipped in a known way for adding of acid or caustic during the growth to regulate the pH in the area of 4,0-6,0, preferably about 4.5. The fermentation is preferably conducted at a temperature between 40°-50° C., more preferably about 45° C. Equipment used for growing of *Rhizomucor pusillus* is sterilized beforehand, and aseptic tecniques are used in connection with the fermentation. Fermentation is preferably finished in 2-4 days.

The Support of Air

It will be of vital importance for the yield of enzymes that the microorganism is mixed well in the fermenter during the fermentation. It is also of importance that the air or the oxygen which is added to the fermenter is dispersed in the nutrient medium in such a way that there will be aerobic conditions all over the fermenter during the fermentation.

The Design of the Apparatus

During the work leading to the invention it was found that the size and the shape of the fermenter is essential to the yield of the enzyme. It is important that the supplied air or oxygen is distributed all over the fermenter, that the mixing is effective so that the fungus is also smoothly distributed during the fermentation and does not scale on the fermenter walls and in the pipe systems and that the conditions inside the fermenter are aerobic all the time. Reference is made to Examples 1 and 5 in the following, where Example 1 describes the use of a 7 liter fermenter and Example 5 describes the use of a 300 liter fermenter.

Analysis

The enzyme activity is measured by measuring the rising amount of reducing sugar by means of photometric at 450 nm. The Analysis of reducing sugar follows S. Dygert, L. H. Li, D. Florida and J. A. Thoma, as published in Analytical Biochemistry, Vol. 13 (1965) page 367-374 and described below.

A 5 ml copper-reagent is added to each of 6 eprouvettes. A 5 ml sample of enzyme, temperated at 30° C., is mixed together with 5 ml barley-$\beta$-glucan (also temperated at 30° C.) in a clear eprouvette and 1 ml of the mixture is sucked and added to the first eprouvette with copper-reagent. The time is to be recorded. Then every 5 minutes during a period of 20 minutes a 1 ml sample of the barley-$\beta$-glucan mixture is sucked, which then is added to the idle eprouvettes with copper-reagent. Finally, 1 ml of acetate buffer is added to the sixth and last eprouvette with copper-reagent. A 5 ml neocuproinic-reagent is added to all of the eprouvettes and then all of them are placed on a boiling waterbath for 12 minutes. The eprouvettes are then cooled with cold water and 11 ml of aqua destilata is added to each of them. The content of reducing sugar is measured photometrically at 450 nm against the eprouvette with pure acetate buffer as blank.

The copper-reagent mentioned above is produced by weighing 40.0 g $Na_2CO_3$ and 16.0 g glycine which are soluted in 600 ml aq. dest. When dissolved, 0.45 g $CuSO_4.5 H_2O$ is added and the solution is adjusted to 1000 ml.

The neocuproinic-reagent mentioned above is produced by weighing 1.20 g neocuproin . HCl (2,9-dimethyl-1,10-phenanthrolinehydrochloride) which is dissolved in water and adjusted to 1000 ml.

Barley-$\beta$-glucan solution mentioned above is produced by weighing 0.50 g barley-$\beta$-glucan which is dissolved in 70 ml aq. dest. by heating to 80°-90° C. for 20 minutes. Filtering and the filtrate is added 10 ml 0.5M acetate buffer (pH 4.0). Diluted to 100 ml in a measuring flask and then 0.02 g $NaN_3$ is added.

The acetate buffer is produced by weighing 30.3 g acetic acid which is diluted with appr. 900 ml aq. dest. Then 2.5 g NaOH in solid form is added and the pH is regulated to pH 4.0 with 1N NaOH. Then 0.2 g $NaN_3$ is added and the solution is diluted to 1000 ml.

During the test the concentration of the enzymatic solution has to be regulated so the amount of reducing sugar coming from the barley-$\beta$-glucane is in linearic proportion with the time. When necessary the enzymatic solution is diluted with 0.05M acetate buffer. The enzyme activity is analyzed according to the abovementioned analytic method as reducing sugar with glucose as reference. One enzyme unit (EU) is defined as the amount of enzyme which is giving reducing sugar equivalent 1 $\mu$mol glucose each minute at 30° C.

For better understanding of the invention reference is made to the following examples:

EXAMPLE 1

300 ml of a inoculum of *Rhizomucor pusillus* (Lindt) Schipper CBS 551.82 is added to a fermenter (7 liter) with 5 liter salt medium of the following composition:

| | |
|---|---|
| $KH_2PO_4$ | 2.0 g |
| $MgSO_4 \cdot 7 H_2O$ | 1.75 g |
| $CaCl_2$ | 0.2 g |
| Trace elements solution | 2.5 ml |
| Water | 1.0 l |

The solution of trace elements has the same composition as the solution described above for producing inoculum.

For foam depression Berol 374 (Berol Kemi AB, Sweden) was used. The fermentation was done at pH 5.5 with a temperature of 40° C. and a stirring speed around 600 rpm. The air support was 3 vvm, i.e. 15 liter air/min. to the fermenter.

40 g/liter potato starch was used as C-source and 13.4 g/liter $NH_4Cl$ as N-source. The fermentation time is 67 h. The enzyme activity was 400 EU/liter.

EXAMPLE 2

*Rhizomucor pusillus* (Lindt) Schipper CBS 551.82 was grown on 40.0 g/liter barley flour and fermented under the same conditions as mentioned in Example 1, but the fermentation time was 45 h. The enzyme activity was measured to be 950 EU/liter.

EXAMPLE 3

300 ml of an inoculum with *Rhizomucor pusillus* (Lindt) Schipper CBS 551.82 was fermented under the same conditions as mentioned in Example 2. 7.5 g/liter urea was used as N-source. The enzyme activity was measured to be 870 EU/liter.

EXAMPLE 4

300 ml of an inoculum with *Rhizomucor pusillus* ATCC 22074 was added in a fermenter (7 liter) with 5 liter salt medium as in Example 1 and fermented under the same conditions as in Example 2. The enzyme yield was 170 EU/liter.

EXAMPLE 5

300 ml of an inoculum with *Rhizomucor pusillus* (Lindt) Schipper CBS 551.82 was added in a fermenter (14 liter) with 10 liter salt medium and fermented as in Example 2. These 10 liters were used as inoculum in a fermenter (300 liter) w:th 200 liter salt medium as in Example 1. The fermentation was done in a medium with 40 g/liter barley flour and 13.4 g/liter $NH_4Cl$ at pH 4.7 and a temperature of 40° C. at a stirring speed around 410 rpm. The air support was 0.17 vvm, i.e. 34 liters air/minute to the fermenter. The enzyme activity was 4800 EU/liter after 79 h and 5200 EU/liter after 92 h.

The examples show the following inventable advantages in preference to the use of known micro organisms:

*Rhizomucor pusillus* (Lindt) Schipper CBS 551.82 gives a high yield of enzymes even when the fermenting time is short (2-3 days).

The said micro organism is not sensitive even at high temperatures (40°-50° C.) and low pH (pH approx. 4.0).

The achievement of aerobic conditions all over the fermenter is highly important to get a good yield of enzyme.

We claim:

1. A process for preparation of β-glucanase which comprises:

preparing an inoculum of a species of the fungus *Rhizomucor pusillus* (Lindt) Schipper;

introducing the inoculum and a nutrient medium for the fungus into a fermenter, said nutrient medium containing nutrient salts, trace materials and carbon and nitrogen sources;

fermenting the contents of the fermenter under submersible, aerobic, thermophilic conditions; and isolating β-glucanase from the resultant contents of the fermenter.

2. The process according to claim 1, wherein the species of the fungus is *Rhizomucor pusillus* (Lindt) Schipper CBS 551.82.

3. The process according to claim 1, wherein a starch containing plant flour is used as the carbon source.

4. The process according to claim 3, wherein the weight proportion of carbon to nitrogen is within the range of 3-7.

5. The process according to claim 4, wherein said weight proportion is about 5.

6. The process according to claim 1, wherein an inorganic nitrogen component and/or urea is used as the nitrogen source.

7. The process according to claim 6, wherein the weight proportion of carbon to nitrogen is within the range of 3-7.

8. The process according to claim 7, wherein said weight proportion is about 5.

9. The process according to claim 1, wherein the nutrient medium has a pH between 4.0-6.0.

10. The process according to claim 9, wherein said pH is about 4.5.

11. The process according to claim 1, wherein the fermentation is conducted at a temperature between 40°-50° C.

12. The process according to claim 11, wherein said temperature is about 45° C.

13. The process according to claim 1, wherein the fermentation is finished after 2-4 days, after which the fermentation fluid is separated into a solid part containing the fungus, and a liquid part which contains the β-glucanase.

* * * * *

UNITED STATES PATENT AND TRADEMARK OFFICE
CERTIFICATE OF CORRECTION

PATENT NO. : 4,588,690

DATED : May 13, 1986

INVENTOR(S) : Bernt A. NISSEN and Jon HOVLAND

It is certified that error appears in the above-identified patent and that said Letters Patent is hereby corrected as shown below:

Column 1, line 51, change "No. 2 048 237" to --No. 2 408 237--.

Signed and Sealed this

Fourteenth Day of October, 1986

[SEAL]

*Attest:*

DONALD J. QUIGG

*Attesting Officer*   *Commissioner of Patents and Trademarks*